US012004991B2

(12) United States Patent
Tretheway et al.

(10) Patent No.: US 12,004,991 B2
(45) Date of Patent: Jun. 11, 2024

(54) OSTOMY APPLIANCE

(71) Applicant: SALTS HEALTHCARE LIMITED, Birmingham (GB)

(72) Inventors: Lee Tretheway, Birmingham (GB); Iain Powner, Birmingham (GB); Lee Howard, Birmingham (GB); Jesus Alfaro, Birmingham (GB)

(73) Assignee: SALTS HEALTHCARE LIMITED, Birmingham (GB)

( * ) Notice: Subject to any disclaimer, the term of this patent is extended or adjusted under 35 U.S.C. 154(b) by 642 days.

(21) Appl. No.: 16/649,126

(22) PCT Filed: Sep. 21, 2018

(86) PCT No.: PCT/GB2018/052690
§ 371 (c)(1),
(2) Date: Mar. 19, 2020

(87) PCT Pub. No.: WO2019/058126
PCT Pub. Date: Mar. 28, 2019

(65) Prior Publication Data
US 2020/0289308 A1 Sep. 17, 2020

(30) Foreign Application Priority Data
Sep. 22, 2017 (GB) ...................................... 1715394

(51) Int. Cl.
*A61F 5/448* (2006.01)
*A61F 5/44* (2006.01)
*A61F 5/441* (2006.01)

(52) U.S. Cl.
CPC .............. *A61F 5/448* (2013.01); *A61F 5/441* (2013.01)

(58) Field of Classification Search
CPC ............. A61F 5/448; A61F 5/441; A61F 5/44
See application file for complete search history.

(56) References Cited

U.S. PATENT DOCUMENTS 3,780,739 A * 12/1973 Frank ..................... A61F 5/4405
604/350
3,841,332 A * 10/1974 Treacle ................... A61F 5/445
604/335

(Continued)

FOREIGN PATENT DOCUMENTS

EP 1068848 B1 10/2004
EP 2229924 A1 9/2010

(Continued)

OTHER PUBLICATIONS

Intellectual Property Office Great Britain, "Search Report" in application No. GB2112713.9 dated Sep. 16, 2021, 1 page.

(Continued)

*Primary Examiner* — Guy K Townsend
(74) *Attorney, Agent, or Firm* — Hickman Becker Bingham Ledesma LLP

(57) ABSTRACT

An ostomy appliance for receiving waste is described including: first and second walls connected to each other at or near their peripheries, the first wall having a stoma-receiving opening; a waste collecting cavity defined between the first and second walls; a first weld portion positioned to one side of the appliance and which connects the first and second walls together, which first weld portion extends away from a periphery of the appliance and downwardly towards a bottom of the appliance; and a second weld portion positioned on an opposite side of the appliance to the first weld portion and which connects the first and second walls together, which second weld portion extends away from a periphery of the appliance and downwardly towards a bottom of the appliance.

19 Claims, 6 Drawing Sheets

(56) References Cited

U.S. PATENT DOCUMENTS

| | | | | |
|---|---|---|---|---|
| 4,084,590 | A | * | 4/1978 | Caraway .................. A61F 5/445 604/350 |
| 4,300,560 | A | * | 11/1981 | Steer ........................ A61F 5/445 222/530 |
| 4,519,797 | A | * | 5/1985 | Hall ......................... A61F 5/445 604/339 |
| 4,604,095 | A | * | 8/1986 | Samuelsen ............ A61F 5/4405 604/350 |
| 6,685,684 | B1 | * | 2/2004 | Falconer ................. A61F 5/451 604/355 |
| 7,476,220 | B2 | * | 1/2009 | Lillegaard ............. A61F 5/4404 604/338 |
| 8,562,578 | B2 | * | 10/2013 | Richmann ............. A61F 5/4405 604/335 |
| 9,119,727 | B2 | * | 9/2015 | Hannan ................... A61F 5/445 |
| 9,962,282 | B2 | * | 5/2018 | Chang ..................... A61F 5/445 |
| 9,993,363 | B2 | * | 6/2018 | Masters ................... A61F 5/441 |
| 10,285,847 | B2 | * | 5/2019 | Lesko ...................... A61F 5/441 |
| 10,478,329 | B2 | * | 11/2019 | Oberholtzer ............ A61F 5/445 |
| 10,478,330 | B2 | * | 11/2019 | Wiltshire ................ A61F 5/445 |
| 2003/0014023 | A1 | * | 1/2003 | Kanbara .................. A61F 5/445 604/333 |
| 2009/0163883 | A1 | * | 6/2009 | Christensen ............ A61F 5/441 604/328 |
| 2011/0190718 | A1 | * | 8/2011 | Wheaton ................. A61F 5/445 604/332 |
| 2013/0053802 | A1 | * | 2/2013 | Maidl ...................... A61F 5/445 604/332 |
| 2013/0085463 | A1 | * | 4/2013 | Lesko ...................... A61F 5/441 604/333 |
| 2015/0320585 | A1 | * | 11/2015 | Fattman ................. A61F 5/4407 604/344 |
| 2015/0359657 | A1 | * | 12/2015 | Argent .................... A61F 5/445 604/332 |
| 2016/0058604 | A1 | * | 3/2016 | Wiltshire ............. A61F 5/4404 604/335 |
| 2020/0289308 | A1 | * | 9/2020 | Tretheway ............. A61F 5/448 |

FOREIGN PATENT DOCUMENTS

| | | | | |
|---|---|---|---|---|
| EP | 2510910 | A1 | * | 10/2012 ............. A61F 5/443 |
| EP | 2510910 | A1 | | 10/2012 |
| FR | 2431285 | A1 | | 2/1980 |
| GB | 1119568 | A | * | 6/1965 ........... A61F 5/4404 |
| GB | 1119568 | | | 7/1968 |
| GB | 1119568 | A | | 7/1968 |
| GB | 2124086 | A | | 5/1983 |
| GB | 2124086 | A | | 2/1984 |
| GB | 2214086 | A | * | 3/1985 ............. A61F 5/445 |
| GB | 2149306 | A | | 6/1985 |
| GB | 2268882 | A | * | 1/1994 ............. A61F 5/445 |
| GB | 2394668 | A | * | 5/2004 ........... A61F 5/4404 |
| GB | 2394668 | A | | 5/2004 |
| WO | WO2017079532 | A1 | | 5/2017 |

OTHER PUBLICATIONS

European Patent Office, "Search Report" in EP application No. 22154857.1, dated May 30, 2022, 7 pages.
International Searching Authority, "Written Opinion" in application No. PCT/GB2018/052690, dated, Mar. 28, 2019, 6 pages.
European Patent Office, "Search Report" in application No. PCT/GB2018/052690, dated Mar. 1, 2020, 5 pages.
Patent Examination Report, New Zealand Application No. 762692, dated Jan. 17, 2024, 4 pages.
First official communication, AU Application No. 2018336053, dated Jul. 6, 2023, 7 pages.

* cited by examiner

OSTOMY APPLIANCE

CROSS-REFERENCE TO RELATED APPLICATIONS

The present application is a U.S. national stage application filed under 35 U.S.C. § 371 based upon international patent application number PCT/GB2018/052690 filed Sep. 21, 2018, which claims priority to Great Britain patent application number 1715394.1 filed on Sep. 22, 2017, the entire contents of each of which are hereby incorporated by reference as if fully set forth herein for all purposes.

BACKGROUND

The invention relates to ostomy appliances. In particular, but not exclusively, the invention relates to closed ostomy appliances.

Ostomy appliances are well known. When an ostomy appliance becomes fuller it tends to start to bulge outwardly. Such outward bulging is unsightly, which may cause a user embarrassment. Also, the collection of waste in the bottom of the appliance can cause a user discomfort as it tends to ▯pull▯ at the top of a wafer which connects the appliance to a user. This can lead to the wafer detaching, which is clearly undesirable.

The present invention seeks to address these problems.

SUMMARY

According to a first aspect of the invention we provide an ostomy appliance for receiving waste including:
first and second walls connected to each other at or near their peripheries, the first wall having a stoma-receiving opening;
a waste collecting cavity defined between the first and second walls;
a first weld portion positioned to one side of the appliance and which connects the first and second walls together, which first weld portion extends away from a periphery of the appliance and downwardly towards a bottom of the appliance; and
a second weld portion positioned on an opposite side of the appliance to the first weld portion and which connects the first and second walls together, which second weld portion extends away from a periphery of the appliance and downwardly towards a bottom of the appliance.

Further features of the first aspect of the invention are set forth in the claims appended hereto.

The first and/or second weld portion may be connected to the peripheral connection of the first and second walls.

The first and/or second weld portion may be an extension or continuation of the peripheral connection of the first and second walls.

The first and/or second weld portion may be generally arcuate or a portion thereof may be generally arcuate.

The first and/or second weld portion may be generally curvilinear.

The first and/or second weld portion may be generally elongate.

An end of the first and/or second weld portion remote from the periphery of the appliance may be curved or rounded.

The ostomy appliance may include a plurality of said first weld portions and a plurality of said second weld portions.

The ostomy appliance may include upper and lower first weld portions one positioned above the other, and upper and lower second weld portions one positioned above the other.

The upper first weld portion may be a different shape from a lower first weld portion, and the upper second weld portion may be a different shape from a lower second weld portion.

The upper first weld portion may be smaller in area than a lower first weld portion, and the upper second weld portion may be smaller in area than a lower second weld portion.

The first weld portion may be elongate and have an axis B which extends lengthways thereof substantially midway therethrough, said axis B being inclined at an angle α to an axis C which extends along the peripheral connection of the first and second walls to each other.

Angle α may be less than 90°.

The ostomy appliance may include a further first weld portion positioned closer to a bottom of the appliance that the first weld portion, wherein the further first weld portion may be elongate and have an axis D which extends lengthways thereof substantially midway therethrough, said axis D being inclined at an angle θ to an axis E which extends along the peripheral connection of the first and second walls to each other.

Angle θ may be less than 90°.

Angle θ may be greater than angle α.

The second weld portion may be elongate and have an axis B which extends lengthways thereof substantially midway therethrough, said axis B being inclined at an angle α to an axis C which extends along the peripheral connection of the first and second walls to each other.

Angle α may be less than 90°.

The ostomy appliance may include a further second weld portion positioned closer to a bottom of the appliance that the second weld portion, wherein the further second weld portion may be elongate and have an axis D which extends lengthways thereof substantially midway therethrough, said axis D being inclined at an angle θ to an axis E which extends along the peripheral connection of the first and second walls to each other.

Angle θ may be less than 90°.

Angle θ may be greater than angle α.

The first and/or second weld portion may taper, i.e. narrow in width, as it extends away from the periphery of the appliance and downwardly towards the bottom of the appliance.

According to a second aspect of the invention we provide an ostomy appliance for receiving waste including:
first and second walls connected to each other at or near their peripheries, the first wall having a stoma-receiving opening; and
a waste collecting cavity defined between the first and second walls;
wherein a midline M extends generally vertically between a top and a bottom of the ostomy appliance;
wherein the ostomy appliance further includes:
a first weld portion positioned to one side of the appliance and which connects the first and second walls together, which first weld portion extends away from a periphery of the appliance and downwardly towards the bottom of the appliance;
wherein the first weld portion includes:
a top edge; and
a bottom edge; and
wherein the bottom edge is inclined at an angle to the midline M; and
a second weld portion positioned on an opposite side of the appliance to the first weld portion and which connects the first and second walls together, which second weld portion extends away from a periphery of the appliance and downwardly towards a bottom of the appliance;

wherein the second weld portion includes:
a top edge; and
a bottom edge; and
wherein the bottom edge is inclined at an angle to the midline M.

The second aspect of the invention may include one or more or all of the features of the first aspect of the invention.

According to a third aspect of the invention we provide an ostomy appliance for receiving waste including:
first and second walls connected to each other at or near their peripheries, the first wall having a stoma-receiving opening;
a waste collecting cavity defined between the first and second walls;
a first weld portion positioned to one side of the ostomy appliance and which connects the first and second walls together, which first weld portion extends away from a periphery of the ostomy appliance; and
a second weld portion positioned directly opposite the first weld portion on an opposite side of the ostomy appliance and which connects the first and second walls together, which second weld portion extends away from a periphery of the ostomy appliance;
wherein the first and second weld portions are positioned substantially midway between a top and a bottom of the waste collecting cavity.

The first weld portion may extend downwardly towards a bottom of the appliance and/or the second weld portion may extend downwardly towards a bottom of the appliance.

The third aspect of the invention may include one or more or all of the features of the first aspect and/or the second aspect of the invention.

According to a fourth aspect of the invention we provide an ostomy appliance for receiving waste including:
first and second walls connected to each other at or near their peripheries, the first wall having a stoma-receiving opening;
a waste collecting cavity defined between the first and second walls;
a first weld portion positioned to one side of the appliance and which connects the first and second walls together, which first weld portion extends away from a periphery of the appliance and downwardly towards a bottom of the appliance; wherein the first weld portion includes:
a top edge; and
a bottom edge;
wherein the top edge and bottom edge are generally parallel and are connected by a curved end; and
a second weld portion positioned on an opposite side of the appliance to the first weld portion and which connects the first and second walls together, which second weld portion extends away from a periphery of the appliance and downwardly towards a bottom of the appliance; wherein the second weld portion includes:
a top edge; and
a bottom edge;
wherein the top edge and bottom edge generally parallel and are connected by a curved end.

The fourth aspect of the invention may include one or more or all of the features of any one of the first to third aspects the invention.

According to a fifth aspect of the invention we provide an ostomy appliance for receiving waste including:
first and second walls connected to each other at or near their peripheries, the first wall having a stoma-receiving opening;
a waste collecting cavity defined between the first and second walls;
a first weld portion positioned to one side of the appliance and which connects the first and second walls together, which first weld portion extends away from a periphery of the appliance and downwardly towards a bottom of the appliance;
a second weld portion positioned on an opposite side of the appliance to the first weld portion and which connects the first and second walls together, which second weld portion extends away from a periphery of the appliance and downwardly towards a bottom of the appliance;
a third weld portion positioned to one side of the appliance above the first weld portion and which connects the first and second walls together, which third weld portion extends away from a periphery of the appliance and downwardly towards a bottom of the appliance; and a fourth weld portion positioned on an opposite side of the appliance to the third weld portion and which connects the first and second walls together, which fourth weld portion extends away from a periphery of the appliance and downwardly towards a bottom of the appliance.

The fifth aspect of the invention may include one or more or all of the features of any one of the first to fourth aspects the invention.

According to a sixth aspect of the invention we provide a drainable ostomy appliance for receiving waste including:
first and second walls connected to each other at or near their peripheries, the first wall having a stoma-receiving opening;
a waste collecting cavity defined between the first and second walls;
an outlet which extends away from the stoma-receiving opening, the outlet having a width W and terminating at an opening;
a first weld portion positioned to one side of the appliance and which connects the first and second walls together, which first weld portion extends away from a periphery of the appliance and terminates in a free end; and
a second weld portion positioned on an opposite side of the appliance to the first weld portion and which connects the first and second walls together, which second weld portion extends away from a periphery of the appliance and terminates in a free end;
wherein the distance between the free ends of the first and second welds is greater than the width of the outlet.

The sixth aspect of the invention may include one or more or all of the features of any one of the first to fifth aspects the invention.

According to a seventh aspect of the invention we provide a drainable ostomy appliance for receiving waste including:
first and second walls connected to each other at or near their peripheries, the first wall having a stoma-receiving opening;
a waste collecting cavity defined between the first and second walls;
an outlet which extends away from the stoma-receiving opening, the outlet having a width and terminating at an opening;
a first weld portion positioned to one side of the appliance and which connects the first and second walls together, which first weld portion extends away from a periphery of the appliance; wherein the first weld portion includes:
a top edge; and
a bottom edge;
wherein the top edge and bottom edge are generally parallel and are connected by a curved end; and
a second weld portion positioned on an opposite side of the appliance to the first weld portion and which connects the first and second walls together, which second weld portion extends away from a periphery of the appliance; wherein the second weld portion includes:
a top edge; and
a bottom edge;
wherein the top edge and bottom edge are generally parallel and are connected by a curved end.

The seventh aspect of the invention may include one or more or all of the features of any one of the first to sixth aspects the invention.

According to an eighth aspect of the invention we provide a colostomy appliance for receiving waste including:
first and second walls connected to each other at or near their peripheries, the first wall being provided with a stoma-receiving opening;
a flange or connection member positioned around the stoma-receiving opening;
a waste collecting cavity defined between the first and second walls;
a first weld portion positioned to one side of the appliance below the stoma receiving opening and which connects the first and second walls together, which first weld portion extends away from a periphery of the appliance and downwardly towards a bottom of the appliance; and
a second weld portion positioned on an opposite side of the appliance to the first weld portion below the stoma-receiving opening and which connects the first and second walls together, which second weld portion extends away from a periphery of the appliance and downwardly towards a bottom of the appliance.

The eighth aspect of the invention may include one or more or all of the features of any one of the first to seventh aspects the invention.

According to a ninth aspect of the invention we provide a colostomy or ileostomy appliance for receiving waste including:
first and second walls connected to each other at or near their peripheries, the first wall provided with a stoma-receiving opening;
a flange or connection member positioned around the stoma-receiving opening;
a waste collecting cavity defined between the first and second walls;
a first weld portion positioned to one side of the appliance and which connects the first and second walls together, which first weld portion extends away from a periphery of the appliance and terminates in a free end; and
a second weld portion positioned on an opposite side of the appliance to the first weld portion and which connects the first and second walls together, which second weld portion extends away from a periphery of the appliance and terminates in a free end;
wherein waste is permitted, in use, to pass from the stoma receiving opening directly downwardly to a bottom of the waste collecting cavity between the free ends of the first and second weld portions.

The ninth aspect of the invention may include one or more or all of the features of any one of the first to eighth aspects the invention.

According to a tenth aspect of the invention we provide a colostomy appliance for receiving waste including:
first and second walls connected to each other at or near their peripheries, the first wall provided with a stoma-receiving opening;
a flange or connection member positioned around the stoma-receiving opening;
a waste collecting cavity defined between the first and second walls;
a first weld portion positioned to one side of the appliance and which connects the first and second walls together, which first weld portion extends away from a periphery of the appliance and terminates in a free end which is positioned at a distance $X_1$ or $X_2$ from the periphery of the appliance; and
a second weld portion positioned on an opposite side of the appliance to the first weld portion and which connects the first and second walls together, which second weld portion extends away from a periphery of the appliance and terminates in a free end which is positioned at a distance $Y_1$ or $Y_2$ from the periphery of the appliance;
wherein the free end of the first weld portion is spaced from the free end of the second weld portion by a distance $D_1$ or $D_2$;
wherein a sum of the distances $X_1$ and $Y_1$, or $X_2$ and $Y_2$ is less than the second distance, $D_1$ or $D_2$.

The tenth aspect of the invention may include one or more or all of the features of any one of the first to ninth aspects the invention.

According to an eleventh aspect of the invention we provide a colostomy appliance for receiving waste including:
first and second walls connected to each other at or near their peripheries, the first wall provided with a stoma-receiving opening;
a flange or connection member positioned around the stoma-receiving opening;
a waste collecting cavity defined between the first and second walls;
a first weld portion positioned below the stoma receiving opening and to one side of the appliance and which connects the first and second walls together, which first weld portion extends away from a periphery of the appliance and downwardly towards a bottom of the appliance; and
a second weld portion positioned directly opposite the first weld portion on an opposite side of the appliance to the first weld portion and which connects the first and second walls together, which second weld portion extends away from a periphery of the appliance and downwardly towards a bottom of the appliance.

The eleventh aspect of the invention may include one or more or all of the features of any one of the first to tenth aspects the invention.

Embodiments of the invention will now be described by way of example only with reference to the accompanying drawing, of which:

Referring to the figures, there is shown an ostomy appliance 10 having a top and a bottom generally indicated at 11 and 13, respectively. The ostomy appliance 10 has first and second walls 12, 14 connected to each other at or near their peripheries 15. In the present example the first and second walls 12, 14 are welded to each other. However, they could, alternatively, be adhered to each other or connected using any other suitable means known in the art.

Figure 1:
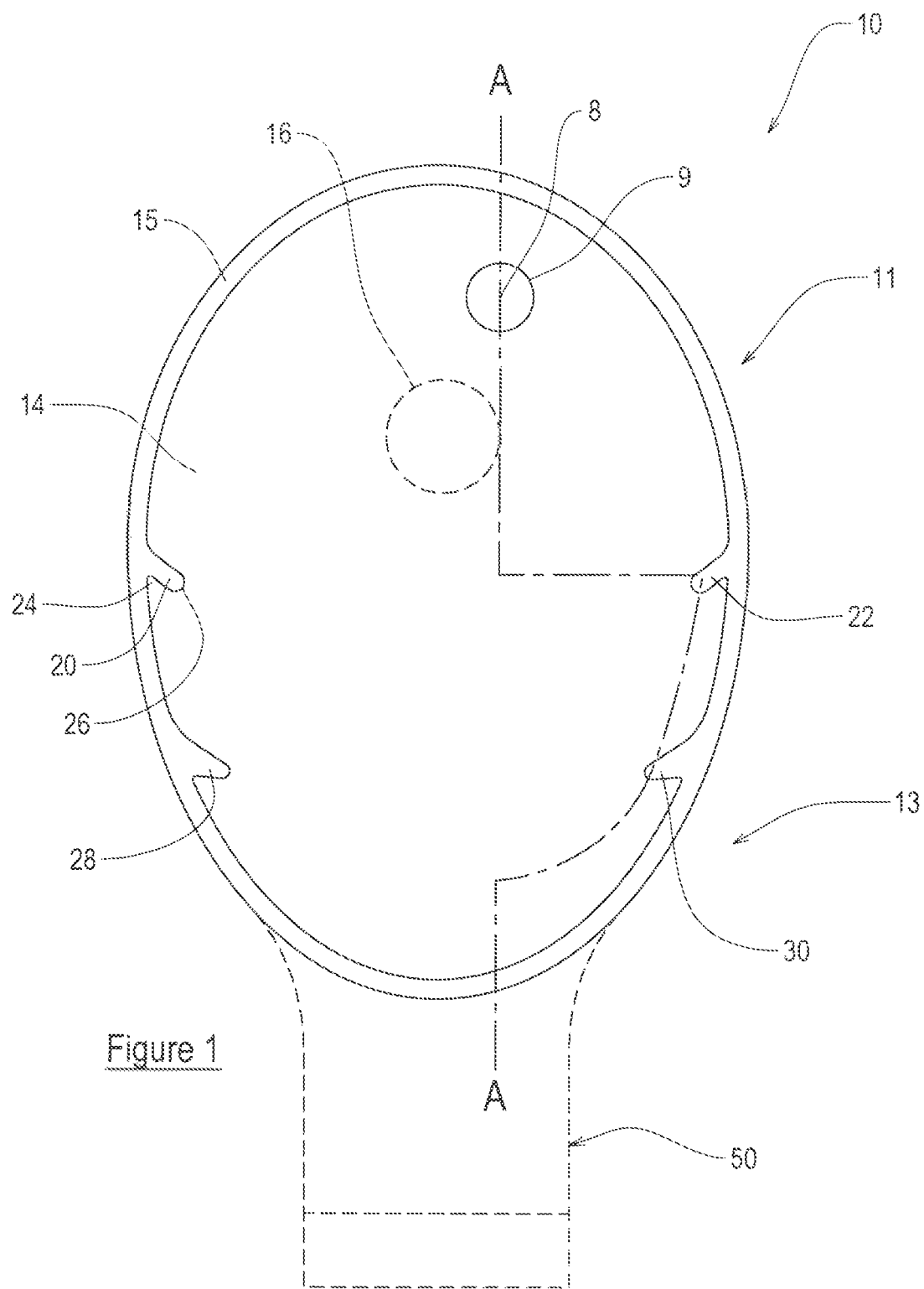
FIG. 1 is a front view of an ostomy appliance in accordance with the present invention.
Figure 2:
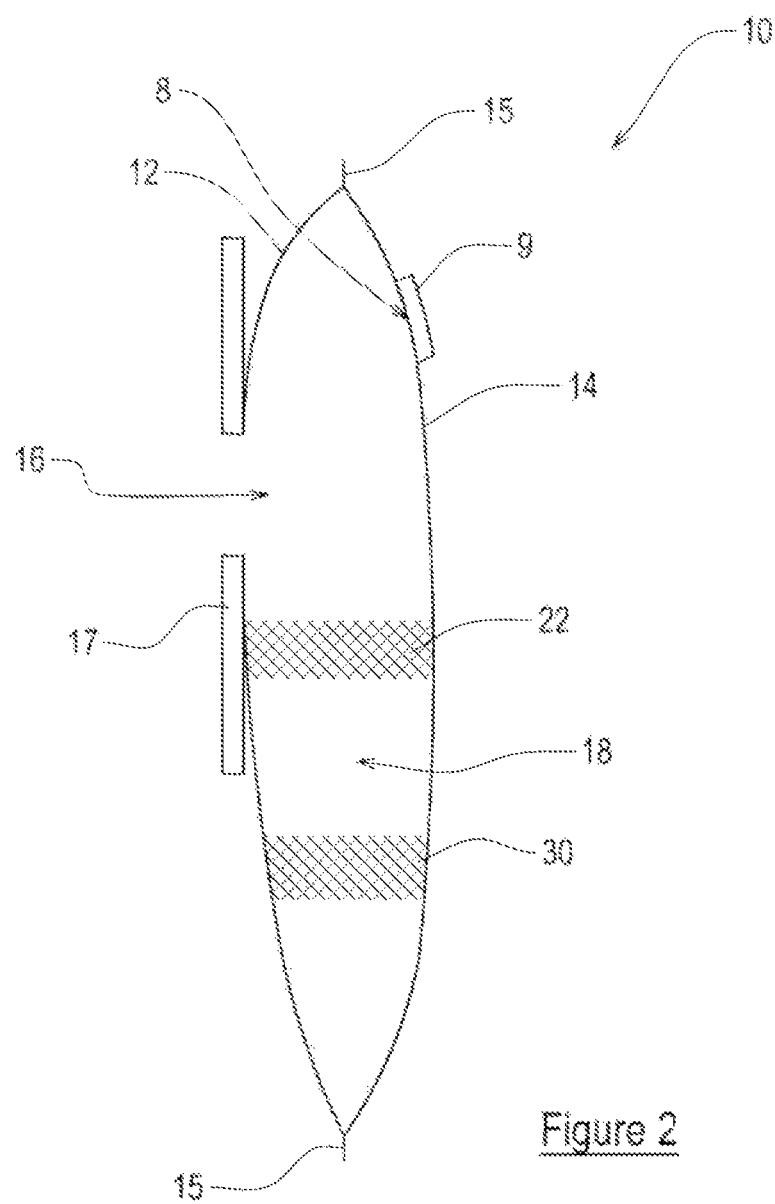
FIG. 2 is a cross-sectional view of the ostomy appliance of FIG. 1 along the line A-A.
Figure 5:
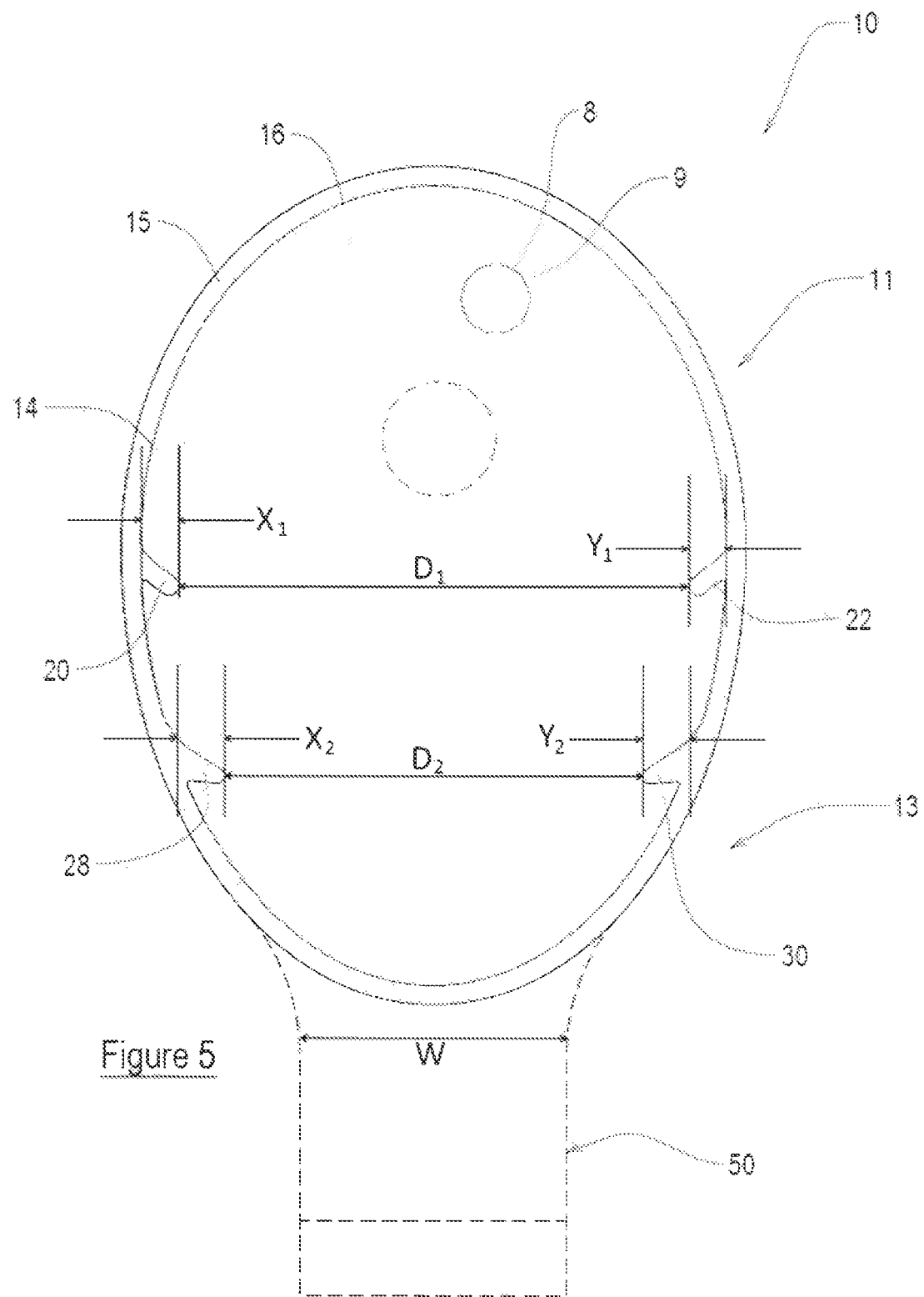
FIG. 5 is a further front view of the ostomy appliance of FIG. 1.

Whilst the appliance shown is a closed colostomy appliance, it could be a drainable ostomy appliance with an outlet 50 such as the one shown in dotted lines in FIG. 1. The outlet 50 may take any suitable form and usually includes a closure mechanism for selective closing/opening the appliance for draining the contents. The outlet 50 may also have a width W, as shown in FIG. 5.

The first wall 12 includes a stoma-receiving opening 16, through which a stoma is received. A connection member or flange 17 is connected to the first wall 12 for attaching the appliance 10 to a user. The connection member 17 used may be, for instance, a hydrocolloid wafer for securing the appliance 10 to the skin of a user around their stoma. Such a configuration is referred to as a one-piece ostomy appliance. Alternatively, the connection member may be for attaching the appliance 10 to a flange for attaching the appliance to a user. Such a device is referred to as a two-piece ostomy appliance. The connection member is positioned around the stoma-receiving opening 16 to ensure a secure fitment of the appliance 10 to a user.

A waste collecting cavity 18 is defined between the first and second walls 12, 14. The first and second walls 12, 14 may be covered by comfort layers though this is not essential. The appliance 10 may also have a filter 9 positioned over a gas vent 8 in either the first wall 12 or second wall 14.

Advantageously, the appliance 10 includes additional weld portions (to the peripheral weld which connects the first and second walls 12, 14 to each other). In the present embodiment, the appliance includes four such additional weld portions D two on each side of the appliance. There are weld portions 20, 28 on the left side of the appliance 10 and weld portions 22, 30 on the right side of the appliance (as viewed in FIG. 1). The weld portions 20 and 22 are positioned directly opposite each other, and the weld portions 28, 30 are positioned directly opposite each other. The weld portion 20 is positioned above the weld portion 28, whilst the weld portion 22 is positioned above the weld portion 30.

Each weld portion 20, 22, 28, 30 extends away from the periphery 15 of the appliance 10 and downwardly towards the bottom of the appliance 10. The weld portions 20 and 22 are positioned at least partly below the stoma-receiving opening 16.

The ostomy appliance is generally symmetrical about the midline M which extends generally vertically between the top 11 and bottom 13 of the ostomy appliance 10, although in other embodiments it need not be.

In this embodiment, and as shown in FIG. 5, the weld portions 20, 22 are positioned completely below the stoma-receiving opening 16, and are positioned substantially midway between the top 11 and the bottom 13 of the appliance 10. In particular the weld portions 20, 22 are halfway between the top 11 and the bottom 13 of the appliance 10. As will be appreciated from FIG. 5, the weld portion 22 is a mirror image of the weld portion 20 about the midline M.

As mentioned above, the weld portions 28, 30 are positioned below the weld portions 20, 22. In particular, the weld portions 28, 30 are positioned substantially midway between the weld portions 20, 22 and the bottom 13 of the appliance 10. In other words, the weld portions 28, 30 are positioned vertically about three quarters of a total length of the appliance 10 away from a top 11 of the appliance 10 and are positioned vertically about one quarter of a total length of the appliance 10 (not including the outlet 50) away from a bottom 13 of the appliance 10. Again, the weld portion 30 is positioned directly opposite the weld portion 28. In particular, the weld portion 30 is a mirror image of the weld portion 28 about the midline M.

The weld portions 20, 22, 28, 30 are highly advantageous in preventing bulging of the appliance 10 during use when it contains waster. The weld portions 20, 22, 28, 30 ensure that the force acting on the appliance as a result of the waste is distributed relatively evenly along the length of the appliance 10. This helps to prevent the appliance 10 from ▯pulling▯ on the top of the connection member 17.

Each weld portion 20, 22, 28, 30 connects the first and second walls 12, 14 to each other and in this embodiment, each weld portion is a continuation of the peripheral weld which connects the first and second walls to each other. Thus, the weld portions 20, 22, 28, 30 are each connected to the peripheral weld 15 and act as an extension or continuation of the peripheral weld 15. This is advantageous because the weld portions 20, 22, 28, 30 may then be formed in the same process which forms the peripheral weld 15 between the first and second walls 12, 14. In alternative embodiments, the weld portions 20, 22, 28, 30 may not be connected to the peripheral connection 15 between the first and second walls 12, 14, e.g. there may be a space between where the first and second walls 12, 14 are not connected to each other.

The weld portions 20, 22, 28, 30 are each elongate with upper edges which are generally arcuate. The weld portions 20, 22, 28, 30 could be curvilinear. An end of the weld portions 20, 22, 28, 30 remote from the periphery 15 of the appliance is curved or rounded.

Figure 3:
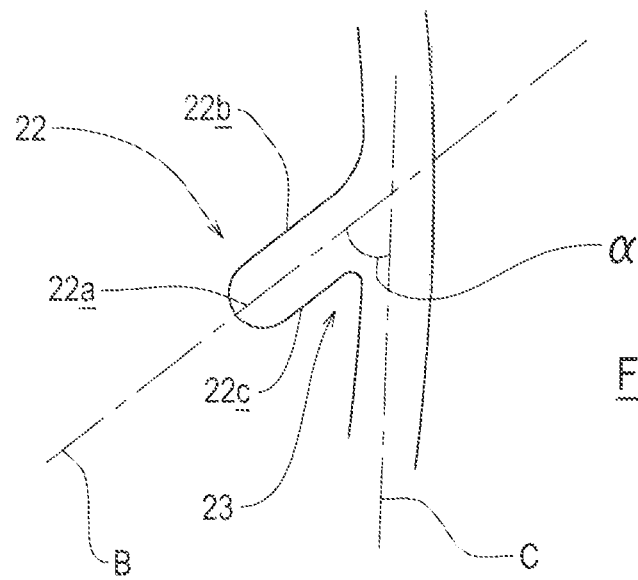
FIG. 3 is a close up view of a first weld portion of the appliance of FIG. 1.
Figure 4:
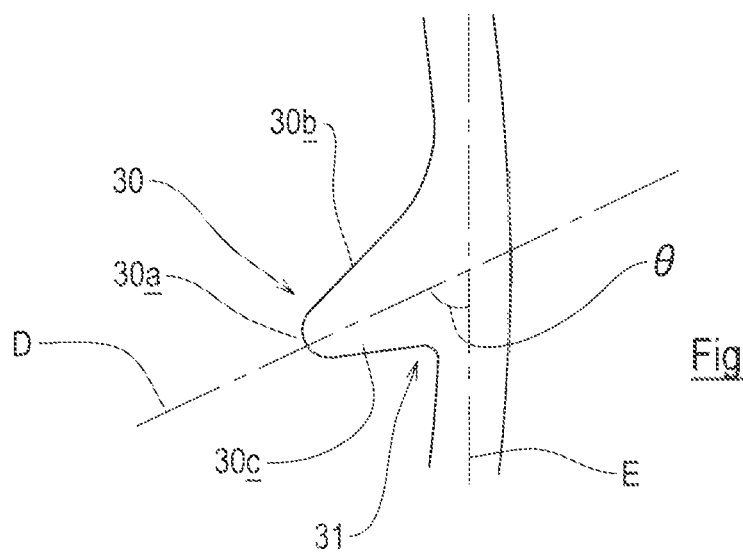
FIG. 4 is a close up view of a further first weld portion of the appliance of FIG. 1.

In particular, and as can be seen in FIGS. 3 and 4, the weld portion 22, 30 has a top edge 22b, 30b and a bottom edge 22c, 30c which are connected by a curved free end 22a, 30a. A portion of the top edge 22b, 30b is parallel with a portion of the bottom edge 22c, 30c. A portion of the top edge 22b, 30b, near the periphery 15, diverges away from the bottom edge 22c, 30c. A portion of the bottom edge 22c, 30c, again near the periphery 15, diverges away from the top edge 22b, 30b. In the present embodiment the portions of the top and bottom edges 22b, 30b, 22c, 30c which diverge are curved, but in other alternative embodiments they may be linear. Again, weld portion 20, 28 is a mirror image of weld portion 22, 30, and so is substantially the same.

The weld portion 20 terminates in a free end 20a which is positioned a distance $X_1$ away from the periphery 15 of the appliance 10. The weld portion 22 also terminates in a free end 22a which is positioned a distance $Y_1$ away from the periphery 15 of the ostomy appliance 10. The free end 20a of the first weld portion is spaced from the free end 22a of the second weld portion by a distance $D_1$, as shown in FIG. 5. A sum of the distances $X_1$ and $Y_1$ is less than the distance $D_1$.

The weld portion 28 terminates in a free end 28a which is positioned a distance $X_2$ away from the periphery 15 of the appliance 10. The weld portion 30 also terminates in a free end 30a which is positioned a distance $Y_2$ away from the periphery 15 of the ostomy appliance 10. The free end 28a of the first weld portion is spaced from the free end 30a of the second weld portion by a second distance $D_2$. A sum of the distances $X_2$ and $Y_2$ is less than the distance $D_2$.

In some embodiments the ostomy appliance 10 is a drainable ostomy appliance and has an outlet 50 having a width W, as explained previously. In those embodiments the distance D1 is greater than the width W of the outlet 50. The distance D2 is also greater than the width W of the outlet 50.

In use, waste is permitted to pass from the stoma-receiving opening 16 between the free ends 20a, 22a, 28a, 30a of the weld portions directly downwardly to a bottom of the waste collecting cavity 18, and in the case of a drainable appliance, directly to the outlet 50.

Figure 7:
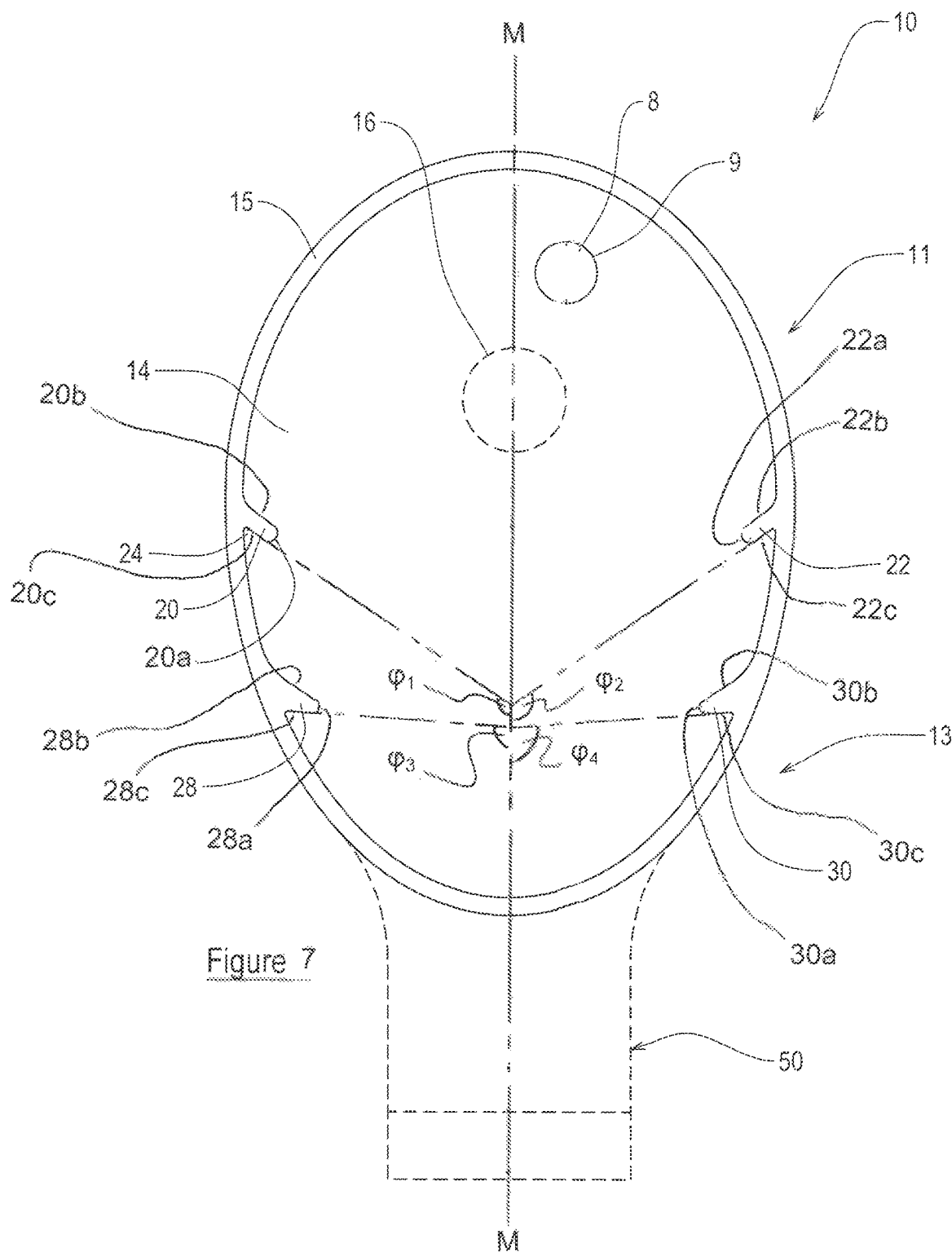
FIG. 7 is a further front view of the ostomy appliance of FIG. 1.

FIG. 7 shows the angle $\varphi_1$, $\varphi_2$, $\varphi_3$, $\varphi_4$ at which the bottom edge of the weld portion 20c, 22c, 28c, 30c is inclined with respect to the midline M.

In the embodiment shown the angles $\varphi_1$ and $\varphi_2$ are the same. However, in other alternative embodiments the angle $\varphi_1$ may be greater than $\varphi_2$, or the angle $\varphi_2$ may be greater than $\varphi_1$ without departing from the scope of the present invention.

The angles $\varphi_3$ and $\varphi_4$ are also the same. However, in other alternative embodiments the angle $\varphi_3$ may be greater than $\varphi_4$, or the angle $\varphi_4$ may be greater than $\varphi_3$.

It can also be seen that the angle $\varphi_1$ is greater than the angle $\varphi_3$. However, in other alternative embodiments the angle $\varphi_1$ may be the same as the angle $\varphi_3$, or the angle $\varphi_3$ may be greater than $\varphi_1$.

Also, the angle $\varphi_2$ is greater than the angle $\varphi_4$. However, in other alternative embodiments the angle $\varphi_2$ may be the same as $\varphi_4$, or the angle $\varphi_4$ may be greater than $\varphi_2$.

Figure 6:
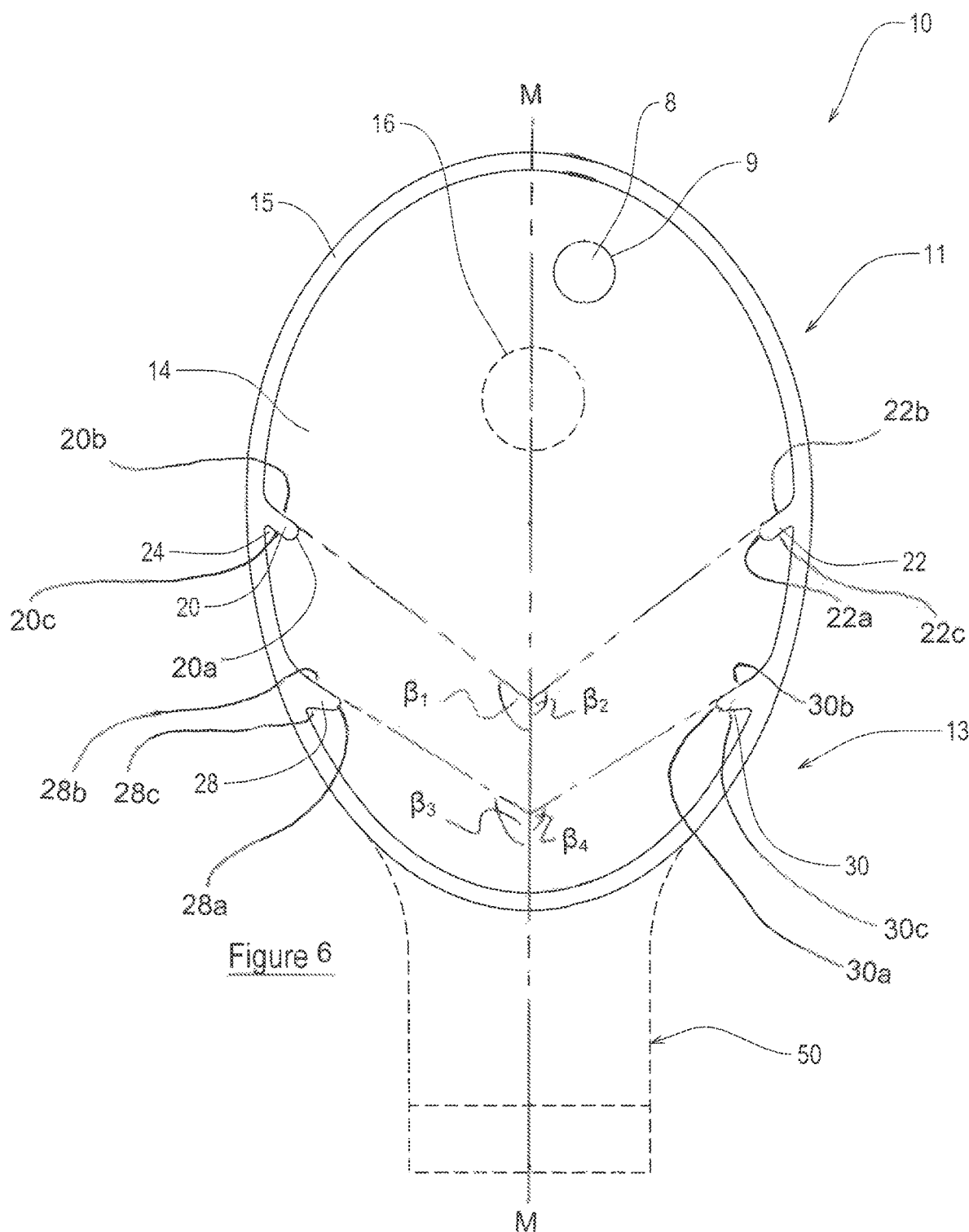
FIG. 6 is a further front view of the ostomy appliance of FIG. 1.

FIG. 6 shows the angle $\beta_1$, $\beta_2$, $\beta_3$, $\beta_4$ at which the top edge of the weld portion 20b, 22b, 28b, 30b is inclined with respect to the midline M.

In the embodiment shown the angles $\beta_1$ and $\beta_2$ are the same. However, in other alternative embodiments the angle $\beta_1$ may be greater than $\beta_2$, or the angle $\beta_2$ may be greater than $\beta_1$ without departing from the scope of the present invention.

The angles $\beta_3$ and $\beta_4$ are also the same. However, in other alternative embodiments the angle $\beta_3$ may be greater than $\beta_4$, or the angle $\beta_4$ may be greater than $\beta_3$.

It can also be seen that the angle $\beta_1$ is greater than the angle $\beta_3$. However, in other alternative embodiments the angle $\beta_1$ may be the same as the angle $\beta_3$, or the angle $\beta_3$ may be greater than $\beta_1$.

Also, the angle $\beta_2$ is greater than the angle $\beta_4$. However, in other alternative embodiments the angle $\beta_2$ may be the same as $\beta_4$, or the angle $\beta_4$ may be greater than $\beta_2$.

In the present embodiment the angle $\beta_1$ is the same as the angle $\varphi_1$. However, in other embodiments the angle $\beta_1$ may be greater than the angle $\varphi_1$. In further envisaged embodiments the angle $\varphi_1$ may be greater than the angle $\beta_1$ without departing from the scope of the present invention.

In the present embodiment the angle $\beta_2$ is the same as the angle $\varphi_2$. However, in other embodiments the angle $\beta_2$ may be greater than the angle $\varphi_2$. In further envisaged embodiments the angle $\varphi_2$ may be greater than the angle $\beta_2$ without departing from the scope of the present invention.

In the present embodiment the angle $\beta_3$ is greater than the angle $\varphi_3$. However, in other embodiments the angle $\beta_3$ may be the same as the angle $\varphi_3$. In further envisaged embodiments the angle $\varphi_3$ may be greater than the angle $\beta_3$ without departing from the scope of the present invention.

In the present embodiment the angle $\beta_4$ is greater than the angle $\varphi_2$. However, in other embodiments the angle $\beta_4$ may be the same as the angle (pa. In further envisaged embodiments the angle $\varphi_4$ may be greater than the angle $\beta_4$ without departing from the scope of the present invention.

As can be seen from FIGS. 3 and 4, the weld portions 20 and 22 are a different shape from the weld portions 28 and 30. It will also be seen from those figures that the weld portions 20 and 22 are smaller in area (i.e. surface area of the weld) than the area of the weld portions 28 and 30. Their shapes and area size have been configured to provide improved resistance to sagging of the appliance 10 during use.

As shown in FIG. 3, the weld portion 22 is elongate and has an axis B which extends lengthways thereof substantially midway therethrough. The axis B is inclined at an angle α (which is preferably less than 90°) to an axis C which extends along the peripheral weld 15. It will be noted that the weld portion 20 is similarly configured to the weld portion 22.

As shown in FIG. 4, the weld portion 30 is also elongate, but it will also be seen that the weld portion 30 tapers, i.e. narrows in width, as it extends away from the peripheral weld 15 downwardly towards the bottom of the appliance 10. The weld portion 30 has an axis D which extends lengthways thereof substantially midway therethrough. The axis D is inclined at an angle θ (which is preferably less than 90°) to an axis E which extends along the peripheral weld 15. It will be noted that the weld portion 28 is similarly configured to the weld portion 30.

Whilst various angles of θ and α fall within the scope of the present invention, further advantages of the operation of the appliance have been found where θ is greater than α. In other words, where the appliance has two or more weld portions at each side, the lower weld portions are inclined at a greater angle to the axis which extends along the peripheral weld 15 than the upper weld portions.

In envisaged embodiments, the appliance 10 may only have one weld portion at each side thereof. In envisaged embodiments, the appliance 10 may have three or more weld portions at each side thereof. In envisaged embodiments, the appliance 10 may an odd number of weld portions at one side of the appliance and an even number of weld portions at the opposite side of the appliance.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A closed colostomy appliance for receiving waste including:
   first and second walls connected to each other at or near their peripheries, the first wall having a stoma-receiving opening;
   a waste collecting cavity defined between the first and second walls;

a first weld portion positioned to one side of the appliance at a periphery of the appliance, wherein at least a portion of the first weld portion connects the first and second walls together at an interior portion of the waste collecting cavity and reduces a width of the waste collecting cavity;

a second weld portion positioned on an opposite side of the appliance to the first weld portion at a periphery of the appliance, wherein at least a portion of the second weld portion connects the first and second walls together at an interior portion of the waste collecting cavity and reduces the width of the waste collecting cavity, wherein the first and second weld portions are not connected directly to each other;

a third weld portion positioned below the first weld portion, wherein at least a portion of the third weld portion connects the first and second walls together at an interior portion of the waste collecting cavity and extends inwardly from a periphery of the appliance in a direction towards the waste collecting cavity; and a fourth weld portion positioned below the second weld portion, wherein at least a portion of the fourth weld portion connects the first and second walls together at an interior portion of the waste collecting cavity and extends inwardly from the periphery of the appliance in a direction towards the waste collecting cavity, wherein the third and fourth weld portions are not connected directly to each other.

2. The closed colostomy appliance according to claim 1 including one or more or all of the following features:
  a) wherein the first and/or second weld portion is connected to the peripheral connection of the first and second walls;
  b) wherein the first and/or second weld portion is an extension or continuation of the peripheral connection of the first and second walls;
  c) wherein the first and/or second weld portion is generally arcuate or a portion thereof is generally arcuate;
  d) wherein the first and/or second weld portion is generally curvilinear;
  e) wherein the first and/or second weld portion is generally elongate;
  f) wherein an end of the first and/or second weld portion remote from the periphery of the appliance is curved or rounded.

3. The closed colostomy appliance according to claim 1 wherein the first weld portion is a different shape from the third weld portion, and wherein the second weld portion is a different shape from the fourth weld portion.

4. The closed colostomy appliance according to claim 3 wherein the third weld portion is smaller in area than the first weld portion, and wherein the fourth weld portion is smaller in area than the second weld portion.

5. The closed colostomy appliance according to claim 1 wherein the first weld portion is elongate and has an axis B that extends lengthways thereof substantially midway therethrough, said axis B being inclined at an angle $\alpha$ to an axis C that extends along the peripheral connection of the first and second walls to each other.

6. The closed colostomy appliance according to claim 5 wherein angle $\alpha$ is less than 90°; or
  wherein the third weld portion is elongate and has an axis D that extends lengthways thereof substantially midway therethrough, said axis D being inclined at an angle $\theta$ to an axis E that extends along the peripheral connection of the first and second walls to each other.

7. The closed colostomy appliance according to claim 6 wherein angle $\theta$ is less than 90° and/or angle $\theta$ is greater than angle $\alpha$.

8. The closed colostomy appliance according to claim 1 wherein the second weld portion is elongate and has an axis B that extends lengthways thereof substantially midway therethrough, said axis B being inclined at an angle $\alpha$ to an axis C that extends along the peripheral connection of the first and second walls to each other, wherein angle $\alpha$ is less than 90°.

9. The closed colostomy appliance according to claim 8 wherein the fourth weld portion is elongate and has an axis D that extends lengthways thereof substantially midway therethrough, said axis D being inclined at an angle $\theta$ to an axis E that extends along the peripheral connection of the first and second walls to each other, wherein angle $\theta$ is less than 90°.

10. The closed colostomy appliance according to claim 9 wherein angle $\theta$ is greater than angle $\alpha$.

11. The closed colostomy appliance according to claim 1 wherein the first and/or second weld portion tapers as it extends away from the periphery of the appliance and downwardly towards the bottom of the appliance.

12. The closed colostomy appliance according to claim 1, wherein a midline M extends generally vertically between a top and a bottom of the closed colostomy appliance;
  wherein the first weld portion includes a first top edge and a first bottom edge and wherein the first bottom edge is inclined at an angle to the midline M; and
  wherein the second weld portion includes a second top edge and a second bottom edge and wherein the second bottom edge is inclined at an angle to the midline M.

13. The closed colostomy appliance according to claim 1, wherein the first and second weld portions are positioned substantially midway between a top and a bottom of the waste collecting cavity.

14. The closed colostomy appliance according to claim 1, wherein the first weld portion includes a first top edge and a first bottom edge, wherein the first top edge and first bottom edge are generally parallel and are connected by a curved end; and
  wherein the second weld portion includes a second top edge and a second bottom edge, wherein the second top edge and the second bottom edge are generally parallel and are connected by a curved end.

15. The closed colostomy appliance according to claim 1 further including a flange or connection member positioned around the stoma-receiving opening, wherein the first weld portion terminates in a first free end, the second weld portion terminates in a second free end, and waste is permitted, in use, to pass from the stoma receiving opening directly downwardly to a bottom of the waste collecting cavity between the free ends of the first and second weld portions.

16. The closed colostomy appliance according to claim 1 wherein the first and second weld portions are positioned below the stoma-receiving opening.

17. The closed colostomy appliance according to claim 1,
  wherein the third weld portion terminates in a third free end;
  wherein the fourth weld portion terminates in a fourth free end; and
  wherein waste is permitted, in use, to pass from the stoma receiving opening directly downwardly to a bottom of the waste collecting cavity between the third free end of the third weld portion and the fourth free end of the fourth weld portion.

18. The closed colostomy appliance according to claim 17, wherein the first free end of the first weld portion is positioned at a distance Xi from the periphery of the appliance;
- wherein the second free end of the second weld portion is positioned at a distance Yi from the periphery of the appliance;
- wherein the first free end of the first weld portion is spaced from the second free end of the second weld portion by a second distance $D_1$; and
- wherein a sum of the distances $X_1$ and $Y_1$, is less than the second distance, $D_1$.

19. The closed colostomy appliance according to claim 18, wherein the third weld portion terminates in a third free end;
- wherein the fourth weld portion terminates in a fourth free end;
- wherein the third free end of the third weld portion is positioned at a distance $X_2$ from the periphery of the appliance;
- wherein the fourth free end of the fourth weld portion is positioned at a distance $Y_2$ from the periphery of the appliance;
- wherein the third free end of the third weld portion is spaced from the fourth free end of the fourth weld portion by a distance $D_2$; and
- wherein the distance, Di is greater than the distance $D_2$.

* * * * *